US010582862B1

(12) United States Patent
Selvaraj (10) Patent No.: US 10,582,862 B1
(45) Date of Patent: Mar. 10, 2020

(54) DETERMINATION AND MONITORING OF BASAL HEART RATE

(71) Applicant: Vital Connect, Inc., Campbell, CA (US)

(72) Inventor: Nandakumar Selvaraj, San Jose, CA (US)

(73) Assignee: Vital Connect, Inc., San Jose, CA (US)

(*) Notice: Subject to any disclaimer, the term of this patent is extended or adjusted under 35 U.S.C. 154(b) by 0 days.

(21) Appl. No.: 14/693,762

(22) Filed: Apr. 22, 2015

(51) Int. Cl.
*A61B 5/024* (2006.01)
*A61B 5/0402* (2006.01)
*A61B 5/11* (2006.01)
*A61B 5/00* (2006.01)

(52) U.S. Cl.
CPC ...... *A61B 5/02438* (2013.01); *A61B 5/02405* (2013.01); *A61B 5/02416* (2013.01); *A61B 5/0402* (2013.01); *A61B 5/11* (2013.01); *A61B 5/7275* (2013.01); *A61B 5/7278* (2013.01)

(58) Field of Classification Search
CPC ............ A61B 5/02438; A61B 5/02405; A61B 5/02416; A61B 5/0402; A61B 5/11; A61B 5/7275; A61B 5/7278
USPC ........ 600/300–301, 509–528, 481, 483, 500, 600/595; 361/679.03
See application file for complete search history.

(56) References Cited

U.S. PATENT DOCUMENTS

| | | | | |
|---|---|---|---|---|
| 4,938,228 A * | 7/1990 | Righter | ............... | A61B 5/0245 600/503 |
| 5,738,104 A * | 4/1998 | Lo | ...................... | A61B 5/02438 600/509 |
| 2005/0177051 A1* | 8/2005 | Almen | ............... | A61B 5/02405 600/509 |
| 2012/0101411 A1* | 4/2012 | Hausdorff | ............. | A61B 5/1117 600/595 |
| 2014/0275854 A1* | 9/2014 | Venkatraman | ......... | A61B 5/721 600/301 |
| 2014/0371610 A1* | 12/2014 | Liu | ...................... | A61B 5/7267 600/509 |
| 2015/0032033 A1* | 1/2015 | Kaufman | ............... | A61B 5/726 600/595 |
| 2015/0088007 A1* | 3/2015 | Bardy | .................. | A61B 5/0022 600/484 |
| 2015/0238140 A1* | 8/2015 | LaBelle | .................. | A61B 5/01 600/508 |

* cited by examiner

Primary Examiner — Gary Jackson
Assistant Examiner — Jonathan Kuo
(74) Attorney, Agent, or Firm — Brundidge & Stanger, P.C.

(57) ABSTRACT

A method and system for continuously monitoring basal heart rate are disclosed. The method comprises detecting a plurality of physiological signals of a user and in response to determining that the user is inactive, filtering the plurality of physiological signals to provide a set of data. The method further includes calculating the basal heart rate of the user using the set of data and an algorithmic process. The system includes at least one sensor to detect a plurality of physiological signals of a user, a processor coupled to the at least one sensor, and a memory device coupled to the processor, wherein the memory device includes an application that, when executed by the processor, causes the processor to carry out the steps of the method.

17 Claims, 7 Drawing Sheets

DETERMINATION AND MONITORING OF BASAL HEART RATE

FIELD OF THE INVENTION

The present invention relates to wearable sensor devices, and more particularly, to continuously determining and monitoring basal heart rate using a wearable sensor device and to predicting cardiovascular health risk factor using the determined basal heart rate.

BACKGROUND

Basal heart rate is the rate at which a human heart pumps blood into the vascular system to meet the oxygen requirement of the human body under normal resting conditions. The basal heart rate is a strong predictor of cardiovascular risks, stress, metabolic rate, developing health issues, athletic training status, and fitness levels. A lower basal heart rate indicates a stronger heart and a healthy cardiovascular system.

Traditional electrocardiogram (ECG) machines are not capable of monitoring heart rate for extended periods of time. Bed-side monitors allow heart rate monitoring only for a limited time duration and under stationary conditions. In addition, continuous ambulatory heart rate monitoring is impossible with traditional ECG sensors. Therefore, there is a strong need for a cost-effective and efficient solution that overcomes the aforementioned issues. The present invention addresses such a need.

SUMMARY OF THE INVENTION

A method and system for continuously monitoring basal heart rate are disclosed. In a first aspect, the method comprises detecting a plurality of physiological signals of a user and in response to determining that the user is inactive, processing the plurality of physiological signals to provide a set of data. The method further includes calculating the basal heart rate of the user using the set of data and an algorithmic process.

In a second aspect, the system includes at least one sensor to detect a plurality of physiological signals of a user, a processor coupled to the at least one sensor, and a memory device coupled to the processor, wherein the memory device includes an application that, when executed by the processor, causes the processor to carry out the steps of the method.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

The present invention relates to wearable sensor devices, and more particularly, to continuously determining and monitoring basal heart rate using a wearable sensor device and to predicting cardiovascular health risk factors using the determined basal heart rate. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Basal heart rate is the rate at which a human heart pumps blood into the cardiovascular circulation of the human body. Factors that affect basal heart rate include body size, physical activity, fitness level, core body temperature, environmental temperature, posture, stress, sleep, and medications. A lower basal heart rate usually indicates a stronger heart and a healthy cardiovascular system. On the other hand, elevated levels of basal heart rate and diminished basal heart rate variability over day and night may indicate cardiovascular health risks.

Therefore, automated and accurate monitoring of the basal heart rate of a person (or patient) that is continuously performed can be very valuable in clinical settings. Specifically, a portable and wearable patient monitoring device with the capability of continuously monitoring basal heart rate as well as instantaneous heart rate for 24-hours in ambulatory conditions can be applied for numerous diagnostic and therapeutic clinical applications.

A method and system in accordance with the present invention can monitor basal heart rate for extended periods of time and is not limited to bed-side monitoring at stationary conditions and for limited time durations. The method and system provide continuous ambulatory monitoring capabilities by providing clinical grade 24-hour electrocardiogram (ECG), heart rate and heart rate variability measurements using a wireless wearable sensor device ("wearable device"). The 24-hour ambulatory basal heart rate monitoring and measurements provided by the method and system in accordance with the present invention can be used for numerous diagnostic and therapeutic applications.

Figure 1:
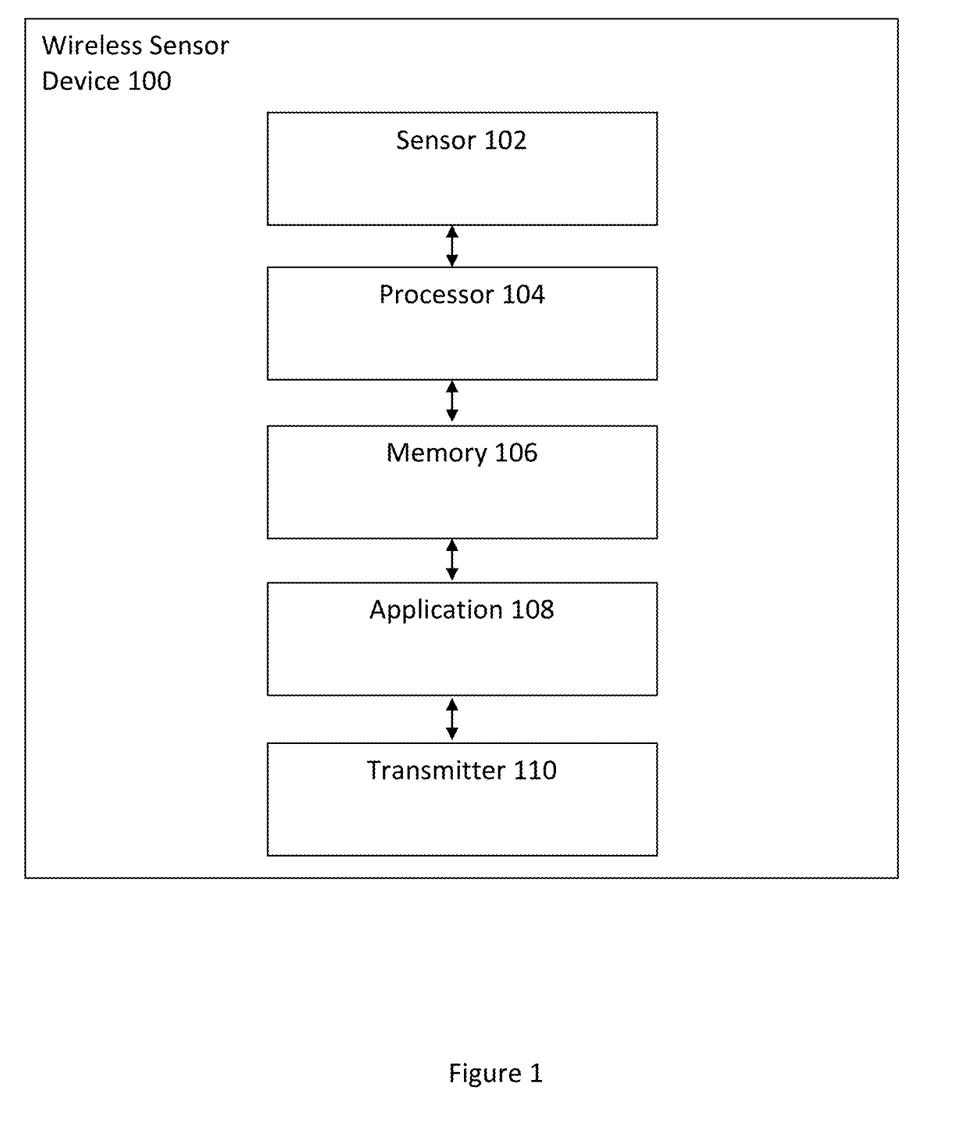
FIG. 1 illustrates a wireless sensor device for continuously monitoring basal heart rate in accordance with an embodiment.

FIG. 1 illustrates a wireless sensor device 100 for continuously monitoring basal heart rate in accordance with an embodiment. The wireless sensor device 100 ("wearable device") includes a sensor 102, a processor 104 coupled to the sensor 102, a memory 106 coupled to the processor 104, an application 108 coupled to the memory 106, and a transmitter 110 coupled to the application 108. One of ordinary skill in the art readily recognizes that the wireless sensor device 100 can include other components and that the components of the wireless sensor device 100 can be coupled in a variety of different ways and that would be within the spirit and scope of the present invention.

In one embodiment, the wireless sensor device 100 is attached to a user to detect various physiological signals via the sensor 102. The sensor 102 obtains the physiological signal data from the user, which is transmitted to the memory 106 and in turn to the application 108 via the processor 104. The processor 104 executes the application 108 to process and analyze the data to obtain health-related information. The information is transmitted to the transmitter 110 and in turn relayed to another user or device for further processing, analysis, and storage. In another embodiment, the transmitter 110 transmits the various detected physiological signals in raw form to a remote device/server (e.g., smartphone, cloud-based server, etc.) for further processing, analysis, and storage.

In one embodiment, the sensor 102 is any of a microelectromechanical systems (MEMS) multi-axial (e.g., tri-axial) accelerometer, an embedded sensor with electrodes, and a photoplethysmography sensor. In one embodiment, the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention.

Additionally, one of ordinary skill in the art readily recognizes that a variety of wireless sensor devices can be utilized including but not limited to wearable devices, a wireless sensor device in a patch form-factor, the Vital Connect Health Patch® wearable device, electrocardiograph devices, smart watches, photoplethysmographs, pulse oximeters, tri-axial accelerometers, uni-axial accelerometers, bi-axial accelerometers, gyroscopes, and pressure sensors and that would be within the spirit and scope of the present invention.

In one embodiment, the HealthPatch® wearable device is a disposable adhesive patch biosensor worn on the chest that incorporates two surface electrodes with hydrogel on the bottom, a battery, an electronic module with an embedded processor and other electronic components and circuitry, a MEMS tri-axial accelerometer, and a Bluetooth Low Energy (BLE) transceiver.

In one embodiment, the wearable device facilitates continuous and automated monitoring of a plurality of physiological signals. In this embodiment, after the wearable device detects the plurality of physiological signals via a plurality of internal and embedded sensors, the electronic module of the wearable device utilizes a plurality of algorithms (e.g., firmware algorithms) to process raw waveforms of the plurality of physiological signals and to transmit a stream of the processed physiological variables via the BLE transceiver/link as encrypted data to a relay such as a smartphone, where the live (real-time) streams of data can be viewed, stored, and analyzed.

To describe the features of the present invention in more detail, refer now to the following description in conjunction with the accompanying Figures.

Figure 2:
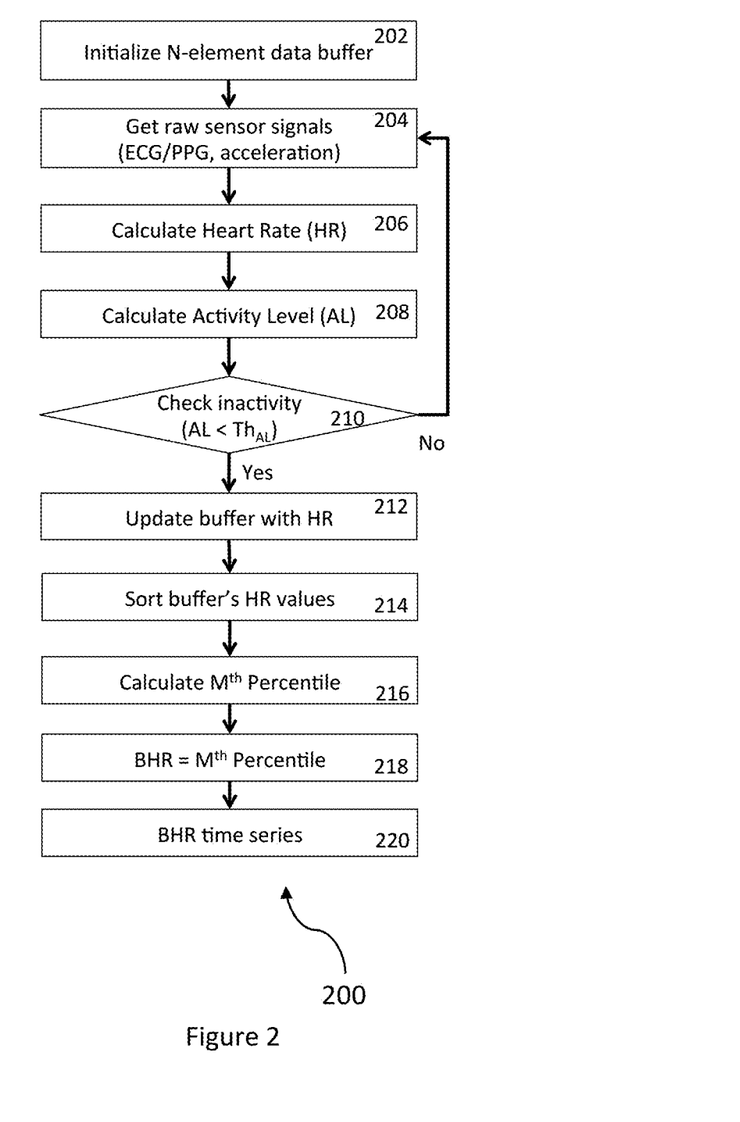
FIG. 2 illustrates a method for continuously monitoring basal heart rate in accordance with a first embodiment.

FIG. 2 illustrates a method 200 for continuously monitoring basal heart rate in accordance with a first embodiment. The method 200 utilizes a percentile algorithmic approach. In the method 200, a data buffer array is initialized with a physical memory of a number (N) of elements, via step 202. The number of elements N of the data buffer array is determined by the duration of the time window used for basal heart rate determination and the sample rate of the heart rate (HR) sensor embedded within the wearable device. For example, if the time window for the basal heart rate determination is assumed to be 30 minutes (mins) and the sample rate of the HR sensor is 1 Hz, then the number of elements N of the data buffer array will be 1800 (N=30× 60×1).

The method 200 includes detecting a plurality of raw physiological signals of a user (patient) including but not limited to electrocardiogram (ECG) or photoplethysmogram (PPG) signals and tri-axial acceleration that are measured by a wearable device that is attached to the user/patient, via step 204. In step 206, firmware or traditional time-domain or any sophisticated parametric/nonparametric model based peak detection algorithms are applied to the inputted ECG/PPG raw signals to detect the R wave peaks in the ECG or the systolic peaks in the PPG. The time durations between the successive R peaks of the ECG or the successive systolic peaks of the PPG are used to obtain instantaneous heart rate (IHR) intervals and heart rate (HR) values. In one embodiment, a low-pass filter is applied to the instantaneous HR (IHR) intervals and the heart rate (HR) values are calculated.

After the heart rate (HR) values have been calculated, signal magnitude area (SMA) values are calculated using one second time windows of band-pass filtered tri-axial body acceleration signals as a sum of the absolute sums of the signal area in 3 axes, per the following equation:

$$SMA = \int_{t}^{t+1} A_x(\tau)d\tau + \int_{t}^{t+1} A_y(\tau)d\tau + \int_{t}^{t+1} A_z(\tau)d\tau, \quad \text{(Equation 1)}$$

where, $A_i$ is the magnitude of the body acceleration in the $i^{th}$ axis and t is time in seconds. After the SMA values are calculated per the Equation 1, the SMA values are normalized to indicate/determine an activity level (AL) of the user, via step 208.

The calculated activity level (AL) is utilized to determine whether the user is active or inactive, via step 210. The calculated activity level indicated by the normalized SMA is compared to a predetermined/learned threshold or coefficient from clinical data $Th_{AL}$ (e.g., $Th_{AL}$=0.1), to determine if the user is active or inactive. If the calculated AL does not satisfy the condition ($AL<Th_{AL}$), the user can be active or in a non-stationary condition, and the method 200 will not include the HR values determined during such active period in the basal heart rate computation and returns back to step 204 to obtain additional raw physiological signals. During active or non-stationary conditions, the previous basal heart rate values calculated during the last rest condition will be held until the condition ($AL<Th_{AL}$) is satisfied or the user becomes inactive.

On the other hand, if the calculated AL satisfies the condition ($AL<Th_{AL}$) and is thus less than the threshold $Th_{AL}$, the user is determined to be inactive. The method 200 proceeds to step 212, where the data buffer array is filled sequentially with the current HR value until the data buffer array is fully utilized or full. Once the data buffer array is full, the first entry of the current data buffer array is removed and then the remaining N−1 elements of the data buffer array are shifted one (1) place to occupy 1-to-(N−1) places of the data buffer array, and the current HR value is placed in the data buffer array at Nth place (like first in first out (FIFO) queue).

The updated data buffer array with the current HR value is utilized for further processing using sorting and percentile calculation. The data buffer array elements are arranged in ascending values of HR (i.e., sorting), via step 214, and the statistical measure $M^{th}$ percentile (e.g., M=16 refers to $16^{th}$ percentile) of the data buffer array's sorted HR values (sorted HR buffer array) is calculated using the HR distribution of the updated data buffer array, via step 216. The percentile can be calculated using a plurality of methodologies including but not limited to the nearest rank method, in which nearest rank 'r' is calculated using N ordered HR values from least to greatest, and the $M^{th}$ Percentile is approximated as the HR value at the order r in the sorted HR buffer array. The nearest rank 'r' is calculated per the following equation:

$$r = \frac{M}{100} \times N, \quad \text{(Equation 2)}$$

where, M is the percentile, N is the number HR values in the data buffer array, and r is the rank of ascending N number of HR values.

The basal heart rate (BHR) value is assigned to be the HR value at the order r in the sorted HR buffer array as an approximation of $M^{th}$ percentile, via step 218. The calculated BHR value will be provided as a BHR time series at the same sampling rate of HR, via step 220. The BHR time series calculated by this algorithm represents the baseline levels of HR series at no activity conditions that can be statistically quantified by the lower percentile levels (e.g., $16^{th}$ percentile) than is mathematically equivalent to [median−1×standard deviation] of HR series.

Figure 3:
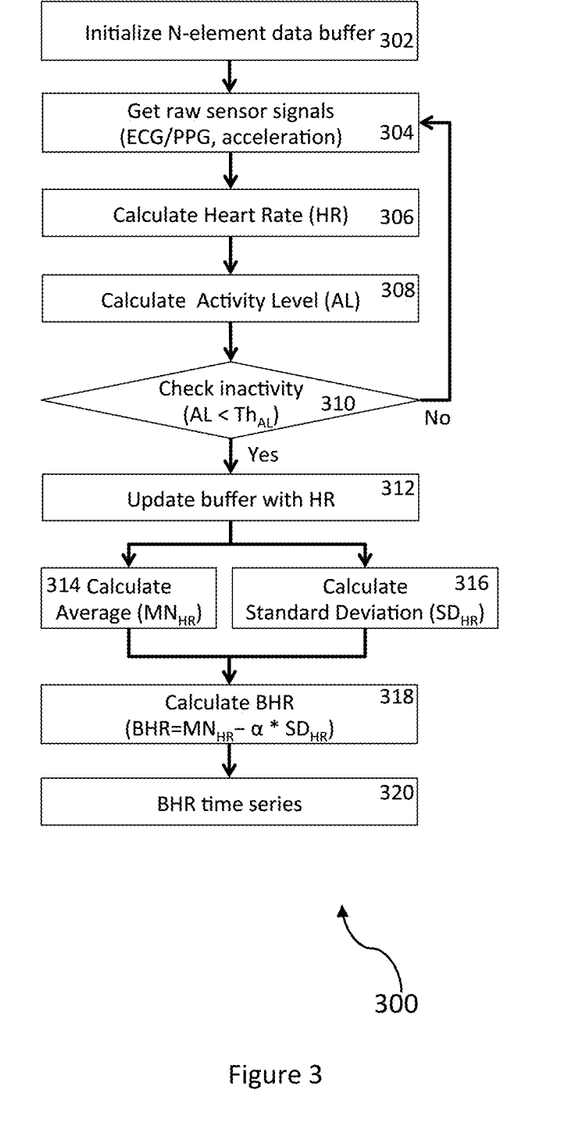
FIG. 3 illustrates a method for continuously monitoring basal heart rate in accordance with a second embodiment.

FIG. 3 illustrates a method 300 for continuously monitoring basal heart rate in accordance with a second embodiment. The method 300 utilizes a moving average and moving standard deviation algorithmic approach. In the method 300, the steps 302-312 of this algorithmic process are identical to the steps 202-212 illustrated by the algorithmic process of the method 200.

After the N-element data buffer array is initialized, the raw sensor signals are detected by the wearable device attached to a user, the heart rate (HR) values are calculated, the activity level (AL) of the user is calculated and compared to a threshold, and the data buffer array is updated accordingly via steps 302-312, the updated data buffer array with the current HR value is utilized for further processing by calculating the moving average and moving standard deviation (SD). In one embodiment, the moving average and the moving standard deviation calculations are carried out using finite impulse response filters via steps 314 and 316, respectively.

In one embodiment, the moving average is calculated, via step 314, per the following equation:

$$MN_{HR} = \frac{\sum_{1}^{N-1} HR_k - HR_1 + HR_N}{N}, \quad \text{(Equation 3)}$$

where, $MN_{HR}$ is the average (mean) value of the HR values of the data buffer array, and N is the number of HR values in the data buffer array. In one embodiment, the moving standard deviation is calculated, via step 316, per the following equation:

$$SD_{HR} = \sqrt{\frac{\left(\sum_{1}^{N-1} HR_k^2 - HR_1^2 + HR_N^2\right) - (N \times MN_{HR}^2)}{N-1}}, \quad \text{(Equation 4)}$$

where, $SD_{HR}$ is the standard deviation, $MN_{HR}$ is the mean of the HR values of the data buffer array, and N is the number of HR values in the data buffer array.

Using the moving average and moving standard deviation values of the HR values of the data buffer array calculated from steps 314 and 316, the method 300 determines the basal heart rate (BHR), via step 318, per the following equation:

$$BHR = MN_{HR} - \alpha \times SD_{HR}, \quad \text{(Equation 5)}$$

where, α is a predetermined/learned coefficient from clinical data (e.g., α=1.0).

The baseline value of HR can be considered as the lowest/minimal value of HR upon which the heart rate variability is observed, as a simple computational approach. However, the basal heart rate estimation using the minimal value of HR data buffer array can be prone to artifacts and outliers. But, both of the aforementioned methods 200 and 300 provide an effective and robust process that minimize the effects of any potential artifacts and outliers in the calculation of the basal heart rate (BHR).

In one embodiment, both the methods 200 and 300 utilize identical preprocessing procedures with the input variables (IHR and AL). The calculated BHR values also would be of similar magnitude in both the methods 200 and 300, because the steps 218 and 318 produce similar results per the statistical viewpoint.

However, the differences between the two methods 200 and 300 are that the BHR value calculated by the method 200 is independent of the HR variability. In other words, the method 200 does not account HR variability into the calculation of the BHR. On the other hand, the method 300 calculated the BHR as a function of HR and its variability (i.e., standard deviation (SD) of HR buffer array), and thus the BHR varies according to the mean and the standard deviation (SD) of HR buffer array. Both the methods 200 and 300 are favorable as they provide for real-time implementation of the respective algorithmic processes.

In one embodiment, the steps of both of the methods 200 and 300 are carried out by embedded processors, modules (e.g., algorithmic signal processing modules), and algorithms of the wearable device and in another embodiment, the steps of both of the methods 200 and 300 are carried out by an external relay (e.g., smartphone, desktop computer, cloud server system, etc.) after the wearable device transmits the detected raw physiological data to the external relay.

Figure 4:
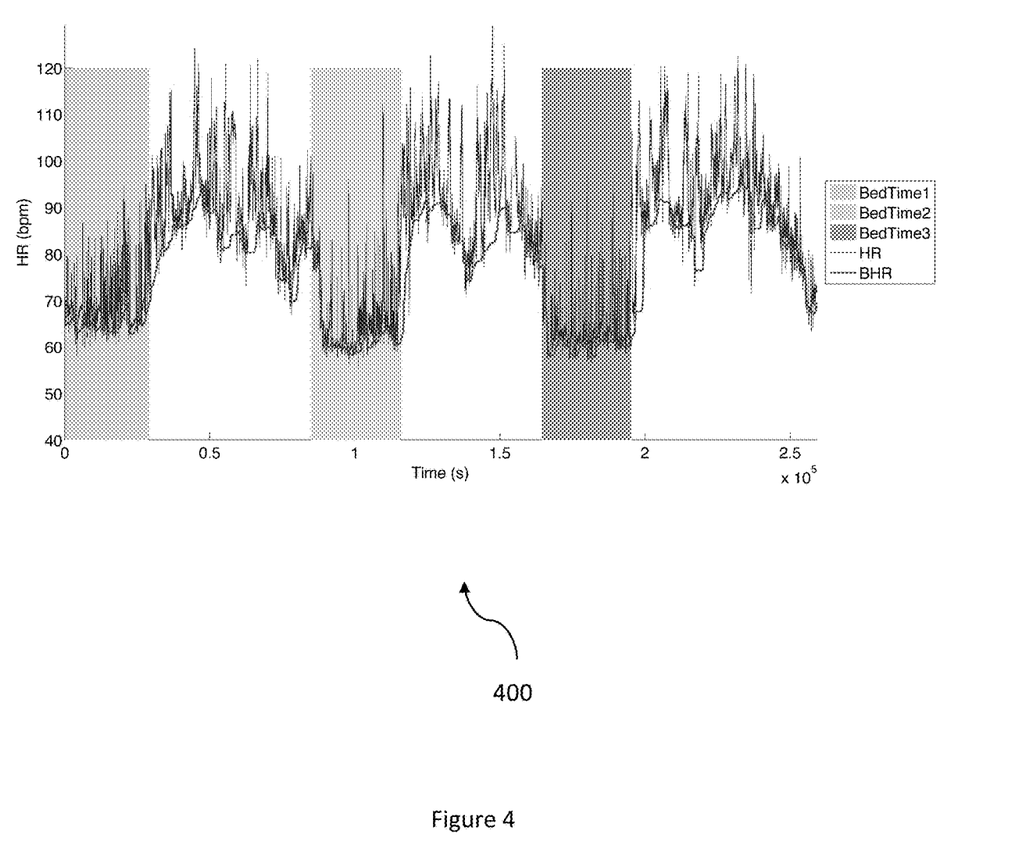
FIG. 4 illustrates a diagram of continuous basal heart monitoring in accordance with an embodiment.

FIG. 4 illustrates a diagram 400 of continuous basal heart monitoring in accordance with an embodiment. The diagram 400 illustrates the continuous changes in magnitude and variability of the basal heart rate (BHR) during bedtime and active-day durations over a predetermined time period by presenting a sample HR time series (thin line) and a BHR time series (thick line) that are obtained from a subject over 3 consecutive days using the method 200.

The BHR time series obtained using the method 300 is very similar and hence not shown by the diagram 400 for simplicity. The shaded parts of the FIG. 4 indicate the time durations when the subject was likely sleeping on a bed during the night (denoted as "BedTime"). The calculated BHR time series tracks the HR time series with the constraint of activity/inactivity and serves as a time varying baseline. Furthermore, as shown in FIG. 4, the magnitude and variability of the BHR is distinctively different during the day and night conditions. Basal heart rate variability in intra-subject and inter-subject can be used for various diagnostic and prognostic applications.

In one embodiment, the determined BHR values of the user can be utilized for a plurality of machine learning based clinical and consumer based applications including but not limited to health risk stratification, fitness analysis, and additional applications. The additional applications can include but are not limited to using the determined BHR values of the user/patient to determine cardiovascular risks/diseases, heart attacks, metabolic disorders, weight management, athletic training, endurance, fatigue, fitness/wellness, acute stress, stress management, core body temperature, hydration levels, therapeutics, sleep quality, relaxation regimes, overall health metrics, and longevity metrics.

Figure 5:
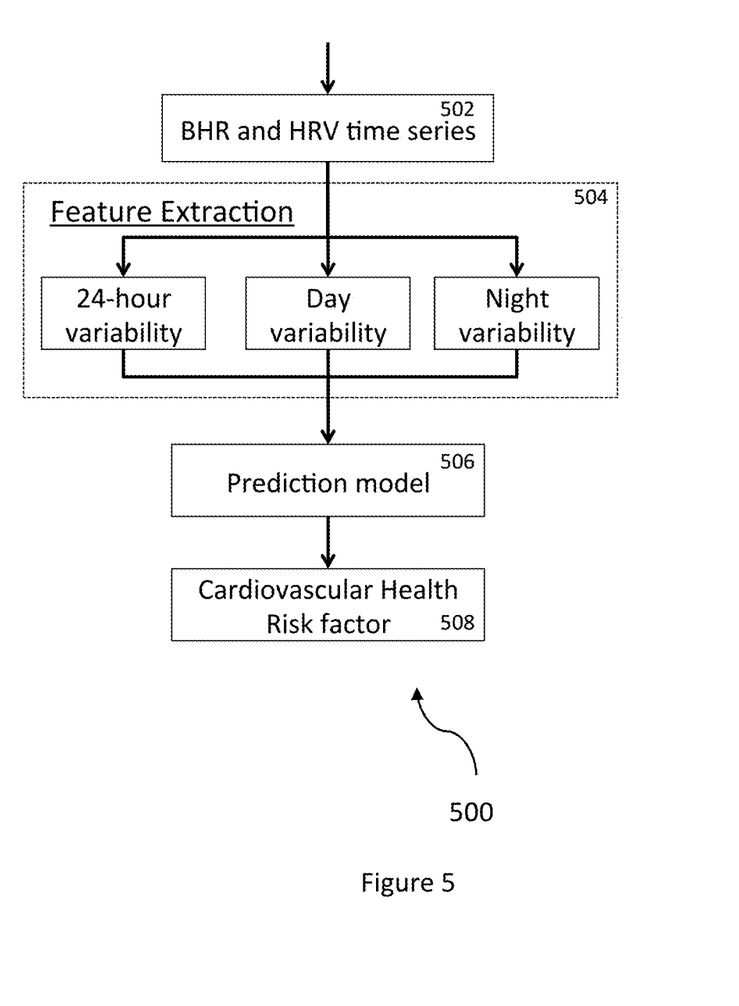
FIG. 5 illustrates a method for predicting cardiovascular health risk using the calculated basal heart rate (BHR) values in accordance with an embodiment.

FIG. 5 illustrates a method 500 for predicting cardiovascular health risk using the calculated basal heart rate (BHR) values in accordance with an embodiment. The method 500 utilizes the BHR values calculated over a 24-hour time period by the methods 200 and 300 including but not limited to the BHR time series and the beat-to-beat HRV time series.

In one embodiment, the steps of both of the methods 500 is carried out by embedded processors, modules (e.g., feature extraction modules, algorithmic process modules), and algorithms of the wearable device and in another embodiment, the steps of the method 500 is carried out by an external relay (e.g., smartphone, desktop computer, cloud server system, etc.) after the wearable device transmits the BHR values/data to the external relay.

The calculated BHR time series and the beat-to-beat HRV time series are input to a machine learning module that prepares the data for feature extraction, via step 502. Both the BHR and the HRV time series have features extracted, via step 504, using a feature extraction module that comprises 3 blocks: 24-hour variability, day-variability, and night-variability. The feature extraction module produces a feature vector (FV). The derived feature vector (FV) is input to a regression/prediction model module, via step 506, and the module predicts the cardiovascular health risk factor of the user/patient, via step 508.

In the feature extraction module of step 504, the entire time series of the 24 hours duration is utilized for the extraction of the features in the 24-hour variability block. On the other hand, the 24-hour time series is split into a day-duration and a bedtime-duration (night duration) by automatically detecting the bedtime and night-time periods when the user is likely sleeping. The segmented HR and BHR time series for the day and the night are processed separately to derive a feature vector for the day-variability block and a feature vector for the night-variability block, respectively.

In step 504, by applying various time series analyses methods to the input time series (BHR and HRV) for 24-hours, day and night segments, the feature vectors $FV_{24\,h}$, $FV_D$ and $FV_N$ are obtained respectively. Furthermore, another feature vector ($FV_P$) is generated using patient health information including but not limited to age in years, gender (female/male), smoking (yes/no), hypertension (yes/no), and physical activity level (low/moderate/intense). In one embodiment, these four sets of feature vectors are combined to form a collective feature vector FV per the following equation:

$$FV = [FV_{24\,h} FV_D FV_N FV_P] \quad \text{(Equation 6).}$$

In another embodiment, additional feature vectors are determined and combined to form the collective feature vector. In one embodiment, the HRV time series are analyzed by the feature extraction module using standard HRV analysis techniques including but not limited to statistical, graphical, and frequency-domain approaches.

The statistical analyses of the HRV time series determines a plurality of features including but not limited to mean, median, standard deviation, range, root mean square successive differences (RMSSD), standard deviation of successive differences (SDSD), number of successive HRV intervals that differ by at least 50 milliseconds (ms) (NN50), proportion of NN50, standard deviation of average of all 5 minute segments of HRV (SDANN), and average of standard deviation of all 5 minute HRV segments (ASDNN).

The geometrical analyses of the HRV time series determines a plurality of features including but not limited to Triangular Index (Triang8), which is the ratio of total number of HRV intervals to the height of the histogram of 8 ms bin width, Triangular interpolation of HRV (TINN8), which is the baseline width of the triangular approximation of HRV distribution, skewness as a measure of symmetry of HRV probability distribution, and kurtosis as a measure of tail and peakedness of HRV distribution relative to a normal distribution.

The frequency domain analyses of the HRV time series determines a plurality of features including but not limited to various frequency band power measures from the power spectral density (PSD) estimation of HRV that include ultra low frequency band power (ULF: <0.003 Hz), very low frequency band power (VLF: 0.003–0.04 Hz), low frequency band power (LF: 0.04–0.15 Hz), high frequency band power (HF: 0.15–0.4 Hz), and total band power (TP: <0.4 Hz).

The analyses of the BHR time series determines a plurality of features including but not limited to mean, median, standard deviation, range, inter-quartile range, skewness, kurtosis, ULF band power and LF band power.

The cardiovascular health (CVH) risk factor is predicted by the feature extraction module using an optimized prediction model and the inputted feature vector FV, via step 508. In one embodiment, the relationship between the feature space and the CVH risk factor is assumed to be linear. Accordingly, the linear regression model can be defined per the following equation:

$$y(x, w) = w_0 + \sum_{j=1}^{M-1} w_j x = w^T x, \quad \text{(Equation 7)}$$

where, x is the input feature space $x=(x_1, \ldots, x_D)^T$, w are model parameters $w=(w_0, \ldots, x_{M-1})^T$, and y is the predicted output. The coefficients of the linear regression model are trained and optimized using clinical trial data or data from a plurality of users to predict the CVH risk factor.

In another embodiment, the relationship between the feature space and the CVH risk factor is assumed to be nonlinear. Accordingly, the nonlinear regression model can be defined per the following equation:

$$y(x, w) = \sum_{j=1}^{M-1} w_j \phi_j(x) = w^T \phi(x), \quad \text{(Equation 8)}$$

where, $\phi(x)$ is the basis function that can include but is not limited to a quadratic polynomial, higher order polynomial, exponential function, radial basis function, and sigmoidal function. The coefficients of the nonlinear regression model are trained and optimized using clinical trial data or data from a plurality of users to predict the CVH risk factor.

Figure 6:
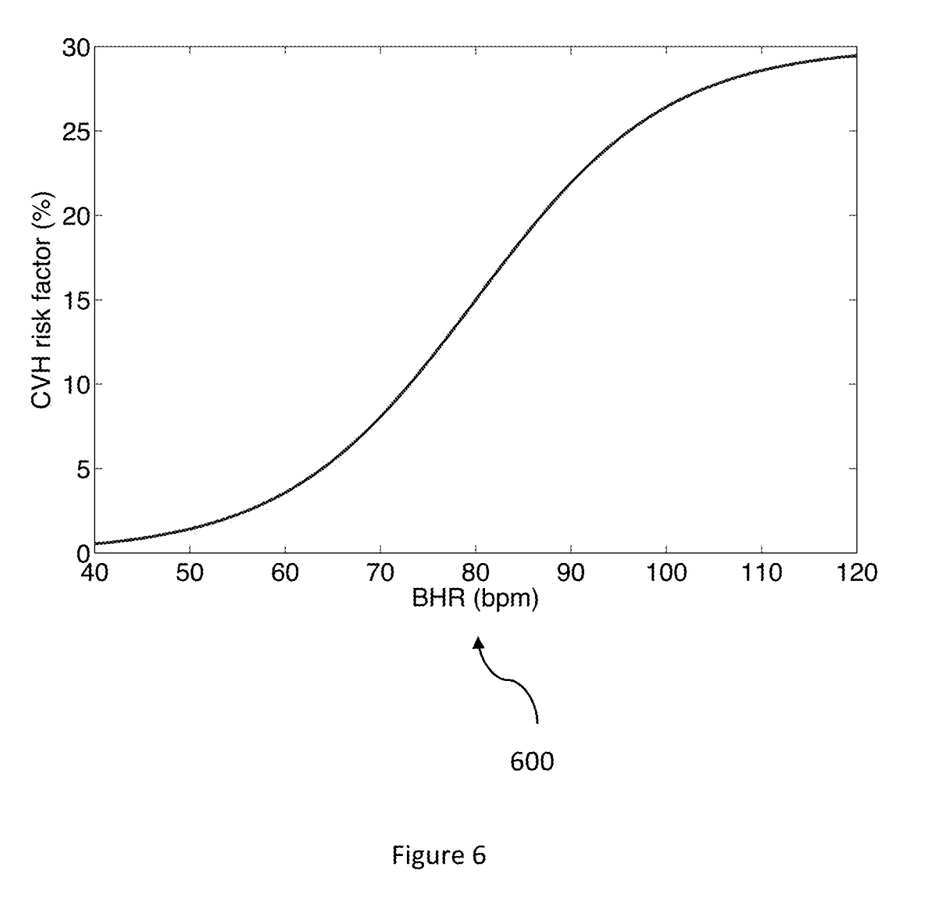
FIG. 6 illustrates a diagram of a nonlinear relationship between the calculated basal heart rate and the predicted cardiovascular health risk factor in accordance with an embodiment.

FIG. 6 illustrates a diagram (i.e., diagram 600) of a nonlinear relationship between the calculated basal heart rate and the predicted cardiovascular health risk factor in accordance with an embodiment. As shown in diagram 600, the nonlinear relationship is based upon an approximation of sigmoidal function. In one embodiment, the basal heart rate (BHR) is calculated using either the method 200 or the method 300 and the predicted cardiovascular health risk factor is calculated using the method 500. Accordingly, the predicted CVH risk factor is low or <3% when the calculated basal heart rate is of low range (~40-60 beats per minute BPM). On the other hand, the predicted CVH risk factor is high or >25% when the calculated basal heart rate is of a high range (~100-120 BPM). Therefore, the lower the basal heart rate and the higher the heart rate variability (HRV), then the lower the CVH risk factor, according to method 500.

In one embodiment, the linear and nonlinear regression models are obtained by machine learning and feature extraction modules utilized by the method 500. The linear and nonlinear regression models can be obtained using a variety of regression analysis tools including but not limited to ordinary least squares, generalized least squares, ridge regression, lasso, and support vector regression. In one embodiment, the optimal parameters of the linear and the nonlinear regression models are determined by an optimization process that utilizes leave-one-out cross validation and minimizes the mean square error of the predicted CVH risk factor values by adjusting the parameter values (e.g., the cost function C in case of linear support vector regression analysis).

Therefore, the method and system in accordance with the present invention provides for the training of the linear/nonlinear regression models using clinical trial data or other aggregated user data, provides for the optimization of the linear/nonlinear regression models to predict the CVH risk factor of the user/patient (wearing the wearable device), and provides for obtaining the optimal regression model coefficients w.

Figure 7:
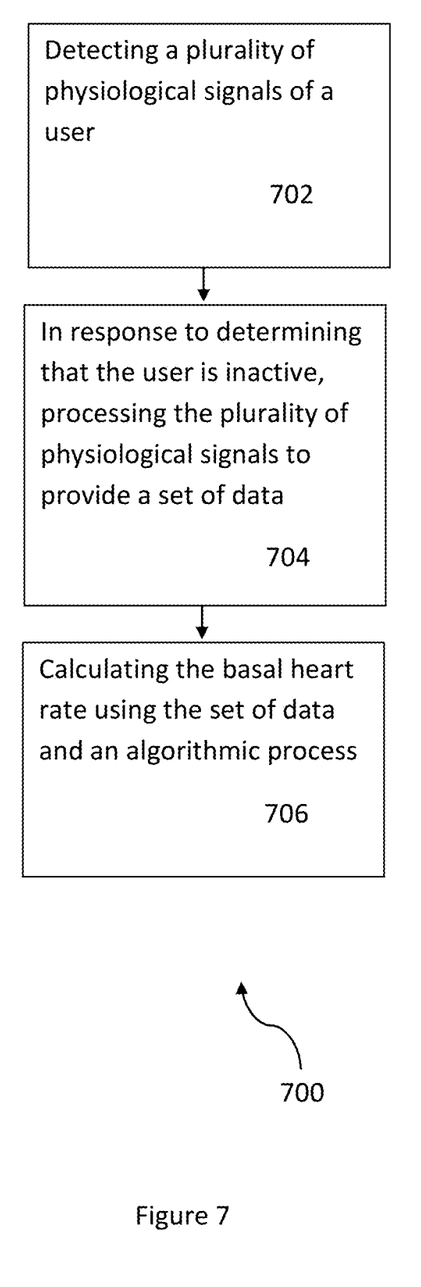
FIG. 7 illustrates a method for continuously monitoring basal heart rate in accordance with an embodiment.

FIG. 7 illustrates a method 700 for continuously monitoring basal heart rate in accordance with an embodiment. The method 700 comprises detecting a plurality of physiological signals of a user, via step 702, in response to determining that the user is inactive, processing (or filtering) the plurality of physiological signals to provide a set of data, via step 704, and calculating the basal heart rate (BHR) of the user using the set of data and an algorithmic process, via step 706.

In one embodiment, the algorithmic process further comprises calculating a predetermined percentile value from the set of data. In one embodiment, the predetermined percentile value is a $M^{th}$ percentile that represents the basal heart rate. Therefore, the basal heart rate of the user is determined by calculating the $M^{th}$ percentile. In another embodiment, the algorithmic process further comprises calculating both a mean (MN) and a standard deviation (SD) of the set of data. The basal heart rate (BHR) is determined/calculated per the following equation: $BHR=MN-\alpha*SD$.

The plurality of physiological signals are detected using a wearable device that is attached to the user. In one embodiment, the wearable device comprises at least one sensor to detect the plurality of physiological signals, a processor coupled to the at least one sensor, and a memory device coupled to the processor, wherein the memory device includes an application. The plurality of physiological signals include but are not limited to heart rate measurements and activity level measurements.

The calculation of the basal heart rate is automated, continuous, and over a predetermined time period. In one embodiment, the predetermined time period is any of 24 hours, 48 hours, and one week. In one embodiment, the filtering step of the method 400 further comprises buffering the set of data and sorting the buffered set of data. The basal heart rate is then calculated using the buffered and sorted set of data and the algorithmic process.

In one embodiment, the calculated basal heart rate is used for a plurality of applications including determining any of cardiovascular risks, cardiovascular diseases, heart attacks, metabolic disorders, energy expenditure, weight management metrics, athletic training measurements, fitness measurements, endurance, fatigue, acute stress, stress management metrics, core body temperature, hydration levels, therapeutics, sleep quality, relaxation regimes, longevity metrics, and overall health metrics. In this embodiment, the method further comprises determining basal heart rate and predicting a cardiovascular health risk factor of the user using the basal heart rate and heart rate variability.

In one embodiment, a system for continuously monitoring basal heart rate comprises at least one sensor to detect a plurality of physiological signals of a user, a processor coupled to the at least one sensor, and a memory device coupled to the processor. The memory device includes an application that, when executed by the processor, causes the processor to: in response to determining that the user is inactive, filter the plurality of physiological signals to provide a set of data, and calculate the basal heart rate using the set of data and an algorithmic process.

As above described, a method and system in accordance with the present invention utilizes a wireless wearable sensor device to automatically, continuously, and accurately monitor basal heart rate measurements of a user/patient throughout the day (day and/or night) and the basal heart rate measurements and data is then utilized to predict the cardiovascular health risk factor of the user/patient. The method and system detect physiological signals related to the user's health and utilize any of a percentile algorithmic process and a moving standard deviation algorithmic process to calculate the basal heart rate (BHR) values (including not limited to basal heart rate and basal heart rate variability). The determined BHR values can also be utilized to analyze the overall health (not just the cardiovascular health) of the user/patient.

A method and system for continuously monitoring basal heart rate has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium (non-transitory). Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for continuously monitoring basal heart rate, the method comprising:
   receiving, by an external relay, a plurality of physiological signals of a user detected by a wearable device, wherein the physiological signals includes: electrocardiogram (ECG) or photoplethysmogram (PPG) signals, and tri-axial acceleration signals;
   calculating, by the external relay, heart rate (HR) values from the electrocardiogram (ECG) or photoplethysmogram (PPG) signals;
   calculating, by the external relay, signal magnitude area (SMA) values using one second time windows of band-pass filtered tri-axial body acceleration signals as a sum of the absolute sums of a signal area in 3 axes;
   normalizing, by the external relay, the SMA values to determine an activity level of the user;
   in response to determining that the user is inactive, calculating, by the external relay, a basal heart rate (BHR) as a function of the calculated HR values and variability of the calculated HR values;
   determining, by the external relay, basal heart rate variability from the calculated basal heart rate;
   extracting, by a feature extraction module of the external relay, features of the calculated basal heart rate and the basal heart rate variability into blocks comprising a 24-hour variability block, a day-variability block, and a night-variability block,
      wherein a time series of a 24-hour duration is utilized for the extraction of the features in the 24-hour variability block,
      wherein the time series of the 24-hour duration is split into a day-duration and a bedtime duration,
      wherein segmented HR and BHR time series for the day-duration and the bedtime duration are processed separately to derive a feature vector for the day-variability block and a feature vector for the night-variability block, respectively;
   inputting, by the external relay, the derived feature vectors in a regression/prediction model module; and
   predicting, by the regression/prediction model module, a cardiovascular health risk factor of the user from the inputted derived feature vectors.

2. The method of claim 1, wherein the calculating the basal heart rate includes calculating a predetermined percentile value from the set of data.

3. The method of claim 2, wherein the predetermined percentile value is a $M^{th}$ percentile.

4. The method of claim 3, wherein the predetermined percentile value is the basal heart rate.

5. The method of claim 1, wherein the calculating the basal heart rate includes calculating the basal heart rate by using a mean (MN) and a standard deviation (SD) of the heart rate values.

6. The method of claim 1, wherein the wearable device is removably attached to the user.

7. The method of claim 6, wherein the wearable device comprises:
   at least one sensor to detect the plurality of physiological signals;
   a processor coupled to the at least one sensor; and
   a memory device coupled to the processor, wherein the memory device includes an application.

8. The method of claim 1, wherein the calculating is automated, continuous, and over a predetermined time period comprising any of 24 hours, 48 hours, and one week.

9. The method of claim 1, further comprises buffering the set of data and sorting the buffered set of data.

10. The method of claim 1, further comprising:
    utilizing the calculated basal heart rate, wherein utilizing the calculated basal heart rate comprises at least one of determining any of cardiovascular risks, cardiovascular diseases, heart attacks, metabolic disorders, energy expenditure, weight management metrics, athletic training measurements, fitness measurements, endurance, fatigue, acute stress, stress management metrics, core body temperature, hydration levels, therapeutics, sleep quality, relaxation regimes, longevity metrics, and overall health metrics.

11. The method of claim 1, wherein the calculating the heart rate (HR) values include applying a parametric/non-parametric model based peak detection algorithm to the ECG or PPG signals to detect R wave peaks in the ECG signal or systolic peaks in the PPG signal.

12. A system for continuously monitoring basal heart rate, the system comprising:
    a wearable device comprising at least one sensor to detect a plurality of physiological signals of a user, a processor coupled to the at least one sensor, and a memory device coupled to the processor, wherein the memory device includes an application that, when executed by the processor, causes the processor to:
       detect a plurality of physiological signals of a user including: electrocardiogram (ECG) or photoplethysmogram (PPG) signals, and tri-axial acceleration signals; and
    an external relay that:
       receives the plurality of physiological signals from the wearable device;
       calculates heart rate (HR) values from the electrocardiogram (ECG) or photoplethysmogram (PPG) signals;
       calculates signal magnitude area (SMA) values using one second time windows of band-pass filtered tri-axial body acceleration signals as a sum of the absolute sums of a signal area in 3 axes;
       normalizes the SMA values to determine an activity level of the user; and
       in response to determining that the user is inactive, calculates a basal heart rate (BHR) as a function of the calculated HR values and variability of the calculated HR values;

determines basal heart rate variability from the calculated basal heart rate;

extracts features of the calculated basal heart rate and the basal heart rate variability into blocks comprising a 24-hour variability block, a day-variability block, and a night-variability block, wherein a time series of a 24-hour duration is utilized for the extraction of the features in the 24-hour variability block, wherein the time series of the 24-hour duration is split into a day-duration and a bedtime duration, wherein segmented HR and BHR time series for the day-duration and the bedtime duration are processed separately to derive a feature vector for the day-variability block and a feature vector for the night-variability block, respectively;

inputs the derived feature vectors in a regression/prediction model module stored in the memory device; and implements the regression/prediction model module to predict a cardiovascular health risk factor of the user.

13. The system of claim 12, wherein the external relay calculates a predetermined percentile value from the set of data.

14. The system of claim 13, wherein the predetermined percentile value is a $M^{th}$ percentile that is the basal heart rate.

15. The system of claim 12, wherein the external relay calculates the basal heart rate by using a mean (MN) and a standard deviation (SD) of the heart rate values.

16. The system of claim 12, wherein the basal heart rate calculation is automated, continuous, and over a predetermined time period including at least one of 24 hours, 48 hours, or one week.

17. The system of claim 12,
wherein the wearable device is removably attached to the user, and
wherein the plurality of physiological signals include heart rate measurements and activity level measurements.

* * * * *